United States Patent
Burnett et al.

(10) Patent No.: US 6,719,740 B2
(45) Date of Patent: Apr. 13, 2004

(54) DELIVERY SYSTEM FOR TOPICAL SKIN CARE AGENTS

(75) Inventors: Katherine M. Burnett, Basking Ridge, NJ (US); Shmuel Dabi, Highland Park, NJ (US); Teresita Diaz, Perth Amboy, NJ (US); Ellen S. Kurtz, Ringoes, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/779,063

(22) Filed: Feb. 8, 2001

(65) Prior Publication Data

US 2001/0047157 A1 Nov. 29, 2001

Related U.S. Application Data

(60) Provisional application No. 60/182,403, filed on Feb. 14, 2000.

(51) Int. Cl.⁷ .......................... A61F 13/00; A61M 35/00
(52) U.S. Cl. ...................................... 604/304; 604/289
(58) Field of Search ................................. 604/304, 305, 604/364, 289–290, 306–308

(56) References Cited

U.S. PATENT DOCUMENTS

| | | | |
|---|---|---|---|
| 3,054,148 A | 9/1962 | Zimmerli | 18/56 |
| 3,394,211 A | 7/1968 | MacDuff | 264/154 |
| 3,929,135 A | 12/1975 | Thompson | 128/287 |
| 4,317,447 A * | 3/1982 | Williams | 424/433 |
| 4,324,246 A | 4/1982 | Mullane et al. | 128/287 |
| 4,342,314 A | 8/1982 | Radel et al. | 128/287 |
| 4,463,045 A | 7/1984 | Ahr et al. | 428/131 |
| 4,572,360 A | 2/1986 | Lischka, geb. Woitzik | 206/0.5 |
| 4,690,679 A * | 9/1987 | Mattingly et al. | 604/383 |
| 4,741,877 A | 5/1988 | Mullane, Jr. | 264/504 |
| 5,006,394 A | 4/1991 | Baird | 428/138 |
| 5,219,340 A | 6/1993 | Seneca | 604/290 |
| 5,300,358 A * | 4/1994 | Evers | 428/422 |
| 5,756,039 A * | 5/1998 | McFall et al. | 264/118 |
| 6,132,841 A * | 10/2000 | Guthrie et al. | 15/104.93 |
| 6,156,323 A | 12/2000 | Verdicchio et al. | 424/401 |

FOREIGN PATENT DOCUMENTS

| | | |
|---|---|---|
| EP | 0 066 463 A1 | 12/1982 |
| EP | 0 336 488 A2 | 10/1989 |

OTHER PUBLICATIONS

Copy of the International Search Report dated Jun. 26, 2001 from corresponding PCT application No. PCT/US01/03969.

* cited by examiner

Primary Examiner—Weilun Lo
Assistant Examiner—C. Lynne Anderson
(74) Attorney, Agent, or Firm—Erin M. Harriman

(57) ABSTRACT

This invention relates to a delivery system which comprises a topical skin care agent, a top layer and a bottom layer where at least one of said top layer and said bottom layer comprises an apertured film having protuberances therein, where said top layer and said bottom layer are attached to each other leaving a pouch between said top layer and said bottom layer, where said protuberances of said apertured film face said pouch, and where said pouch contains said topical skin care agent.

5 Claims, 7 Drawing Sheets

DELIVERY SYSTEM FOR TOPICAL SKIN CARE AGENTS

CROSS-REFERENCE TO RELATED APPLICATIONS

This application claims the benefit under 35 U.S.C. § 119(e) of copending U.S. provisional application Ser. No. 60/182,403, filed Feb. 14, 2000.

BACKGROUND

The skin is said to be the largest organ in the human body. Like other organs of the body, the skin needs care to maintain it in optimal condition and treatment to cure it when it exhibits the symptoms of disease. Often the skin is maintained using skin care products, such as humectants, emollients, and vitamins; and is treated using medicinal agents. Although some agents used to treat the skin are administered orally, many agents are administered topically, and are generally known as topical skin care agents.

When administering topical skin care agents one of the main concerns is the ease of application to such a large organ. One common method of administering such agents to this large surface area consists of bathing the individual in a water bath, which contains the topical skin care agent. Although this method permits easy access to large areas of an individual's skin, it is not without problems. One problem is caused by the fact that many topical skin care agents are not easily dispersed in the bath water. Many of these agents just clump in the bath water and settle to the bottom of the tub. Unfortunately this clumping and settling is unattractive to the user and often the clumping and settling reduces the effect of the topical agent. One such topical agents which is prone to clumping and settling when administered by bath water is oatmeal.

Oatmeal is known to soothe the itching sensation of the skin, which is associated with the common childhood disease, Chicken Pox. Typically a person who is afflicted with Chicken Pox has red itchy and painful "pox type" lesions covering their body. When an infected individual is bathed in a bath containing oatmeal, the itching associated with the lesions is alleviated. Unfortunately, oatmeal is not easily dispersed in water. Powdered bath formulations containing oatmeal are typically formulated with other materials to aid the dispersion of oatmeal into water. Often these powdered formulations may only be added to the bath by sprinkling small portions of the powder under a faucet of running water. Even with this method of adding the powdered formulation, the oatmeal often clumps and settles to the bottom of the bathtub and results in an inferior and incomplete treatment.

An alternate means of adding oatmeal to a bath is the use of an oatmeal bath tablet. Oatmeal bath tablets generally delivers significantly less oatmeal than the process described above.

Therefore, there is a need for a delivery system that provides less mess and more convenience than the current delivery systems for topical medicinal and skin care products. Additionally, because the topical medicinal and skin care products may be solids having small particle sizes, the delivery system should be designed to retain small particle size solids when in the dry state.

Others have attempted to produce delivery systems for applying colloidal oatmeal to a person's skin. For example, U.S. Pat. No. 5,219,340 discloses an applicator for applying a colloidal oatmeal treatment product to a person's skin. The applicator is formed from a porous material including cotton and cotton/polyester blends.

Despite these efforts, there is a continuing need for a delivery system that provides less mess and more convenience than the current delivery systems for topical skin care agents.

SUMMARY OF THE INVENTION

This invention relates to a delivery system for topical skin care agents. This delivery system comprises a topical skin care agent, a top layer and a bottom layer where at least one of said top layer and said bottom layer comprises an apertured film having protuberances therein, where said top layer and said bottom layer are attached to each other leaving a pouch between said top layer and said bottom layer, where said protuberances of said apertured film face said pouch, and where said pouch contains said topical skin care agent.

BRIEF DESCRIPTION OF THE DRAWINGS

FIG. 4 illustrates a cross sectional view of FIG. 1 along line a

DETAILED DESCRIPTION OF THE INVENTION

This invention relates to a delivery system comprising a topical skin care agent, a top layer and a bottom layer where at least one of said top layer and said bottom layer comprises an apertured film having protuberances therein, where said top layer and said bottom layer are attached to each other leaving a pouch between said top layer and said bottom layer, where said protuberances of said apertured film face said pouch, and where said pouch contains said topical skin care agent.

Figure 1:
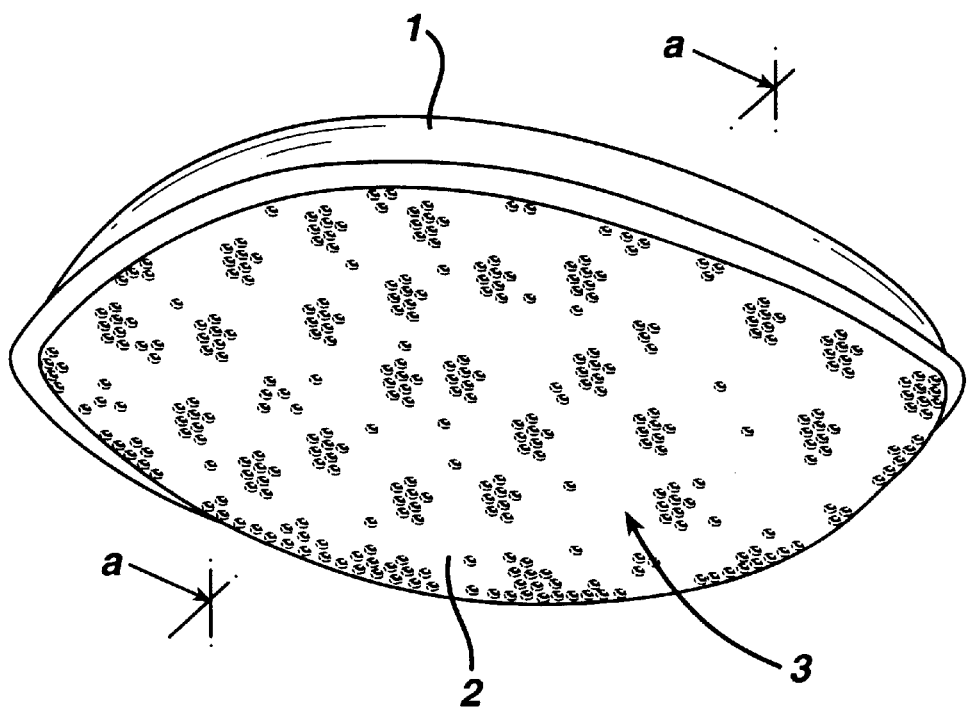
FIG. 1 is a perspective view of a delivery system of the invention.
Figure 6:
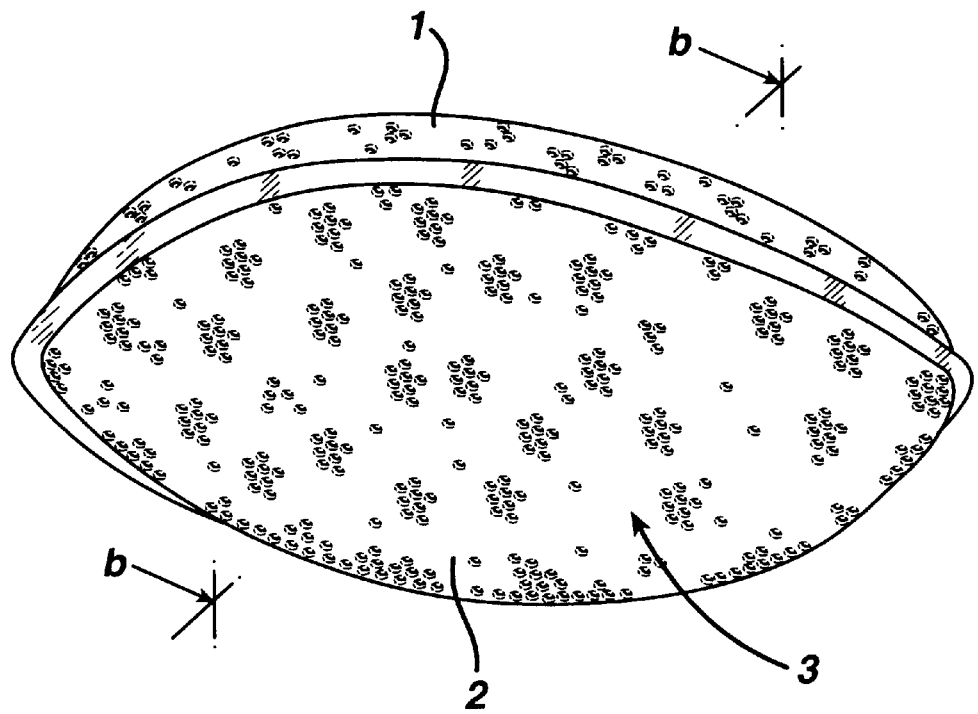
FIG. 6 is a perspective view of an alternate embodiment of the delivery system of the invention.

The delivery systems of this invention are sachet type pouches which are designed to hold topical skin care agents internally intact without leakage of said agents. A perspective view of an exemplary delivery system is illustrated in FIG. 1 and a perspective view of an alternate embodiment of the delivery system is illustrated in FIG. 6. Typically the top layer and the bottom layer are attached by fusing them with heat. Alternatively, these layers may be sewn together or glued with an adhesive. Any method of attachment which allows for the forming of a pouch, 3, which is used to contain a topical skin care agent may be used so long as the method of attachment does not fuse the pouch portion of the delivery system or damage the topical skin care agent.

Figure 2:
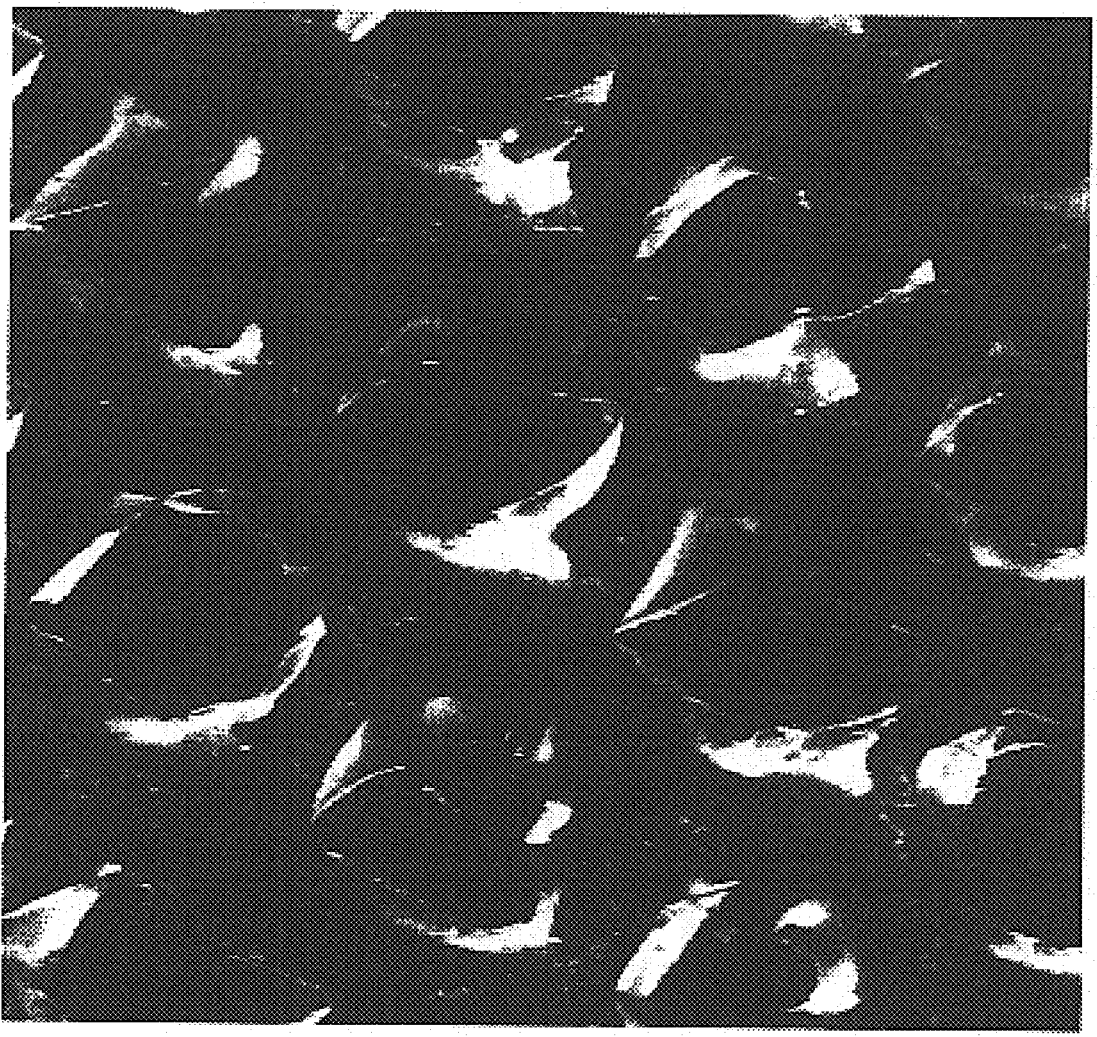
FIG. 2 illustrates the rough side of an apertured film
Figure 3:
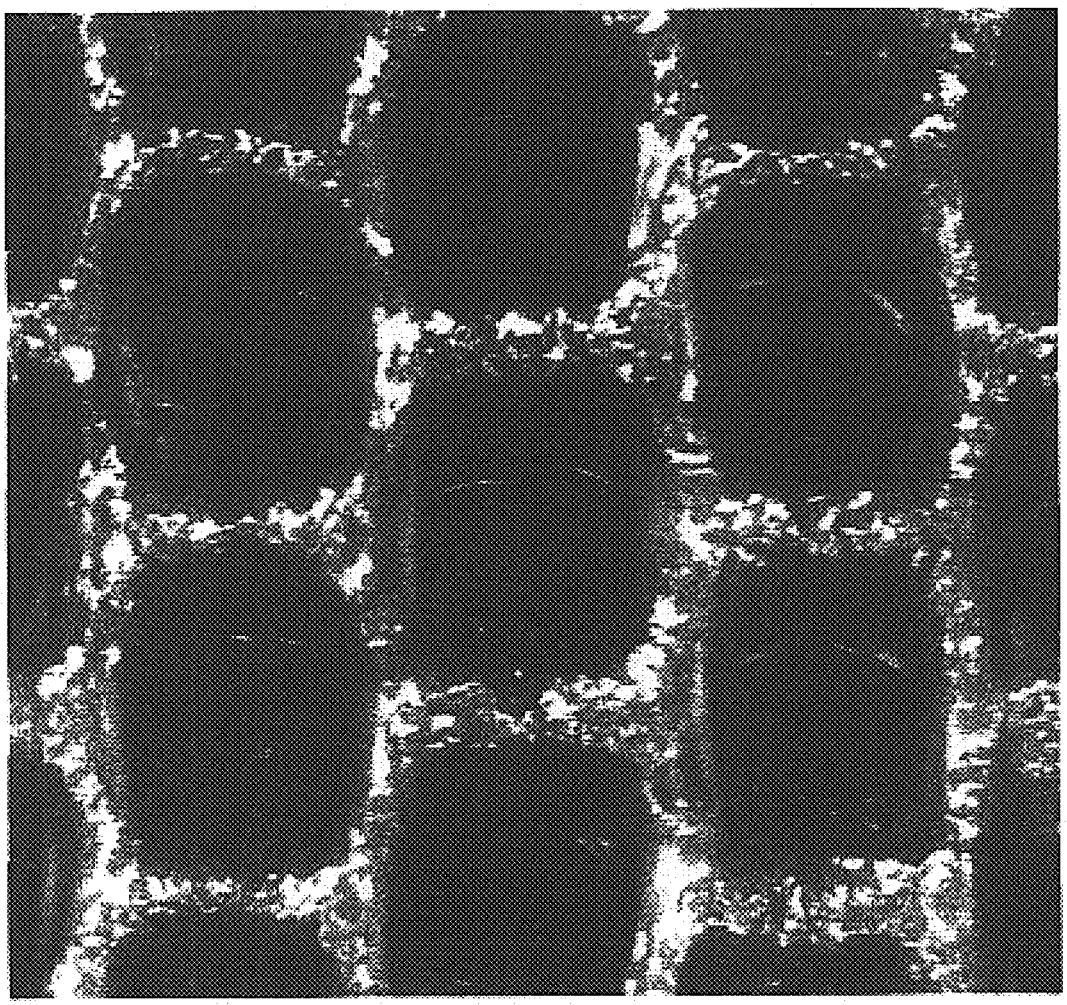
FIG. 3 illustrates the smooth side of an apertured film

At least one layer of the delivery systems of the invention is made of an apertured film. Apertured films are textured films which contain raised protuberances which may be made by a number of methods. Generally speaking, apertured films possess a "rough" side, which contains the raised protuberances as shown in the micrograph of the apertured film in FIG. 2, and an opposing "smooth" side as shown in the micrograph of the apertured film in FIG. 3. By "smooth" side, it is meant the side from which the raised protuberances originate. The protuberances in such apertured films are generally cone-shaped. These films may be made from any polymeric material including, but not limited to polyethylene, metallocene catalyzed polyethylene, polypropylene, and copolymers thereof, and ethylene vinyl acetate copolymers. Such apertured films are disclosed in U.S. Pat. Nos. 3,054,148, 3,394,211, 3,929,135, 4,324,246, 4,342,314, 4,463,045, 4,741,877, and 5,006,394, each of which is hereby incorporated by reference.

The size of the apertures and the number of apertures per square centimeter may vary, depending on the particle size distribution of the topical skin care agent which is being delivered. Generally, if the topical skin care agent is colloidal oatmeal, the size of the apertures in the film may range from 25 microns to 100 microns, preferably from 50 microns to 75 microns. The number of apertures per square centimeter of film may range from 10 to 75, preferably from 15 to 40, more preferably from 20 to 30. The apertured films may contain Microban™ or other suitable anti-bacterial agents in effective amounts. Examples of suitable commercial apertured films include those available from Tredegar Film Products, Inc. under the tradename, "VisPore®," from Polymer Group, Inc. under the tradename, "Reticulon®, or from Guial Inc. under the tradename, "Zeole" with the "VisPore®" film being preferred.

Figure 4:
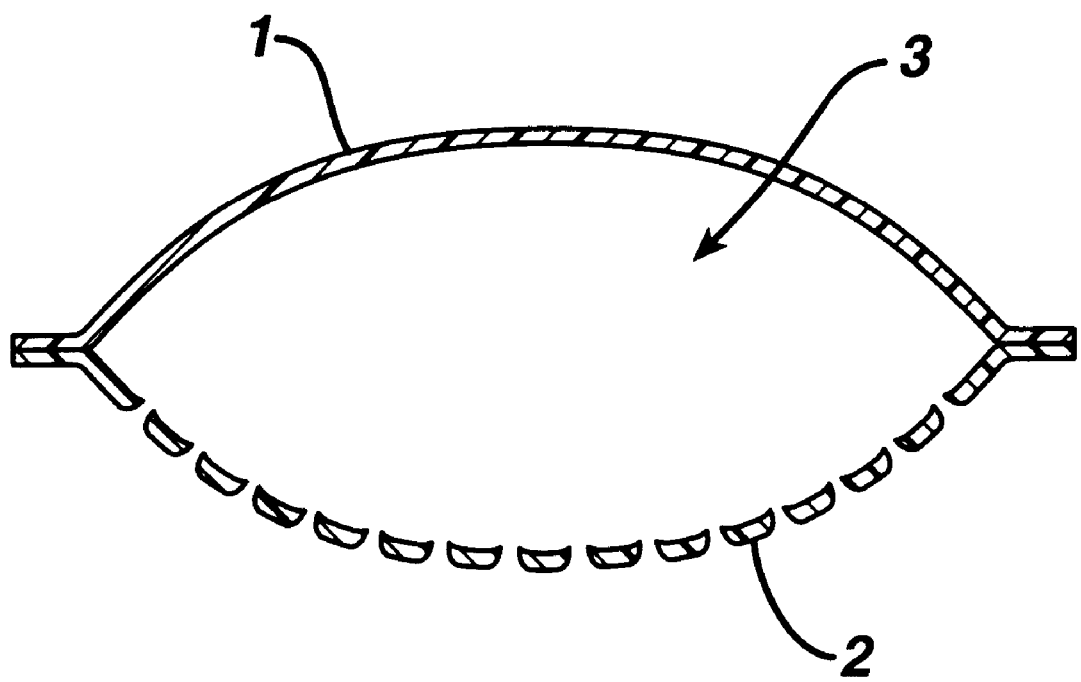
Figure 5:
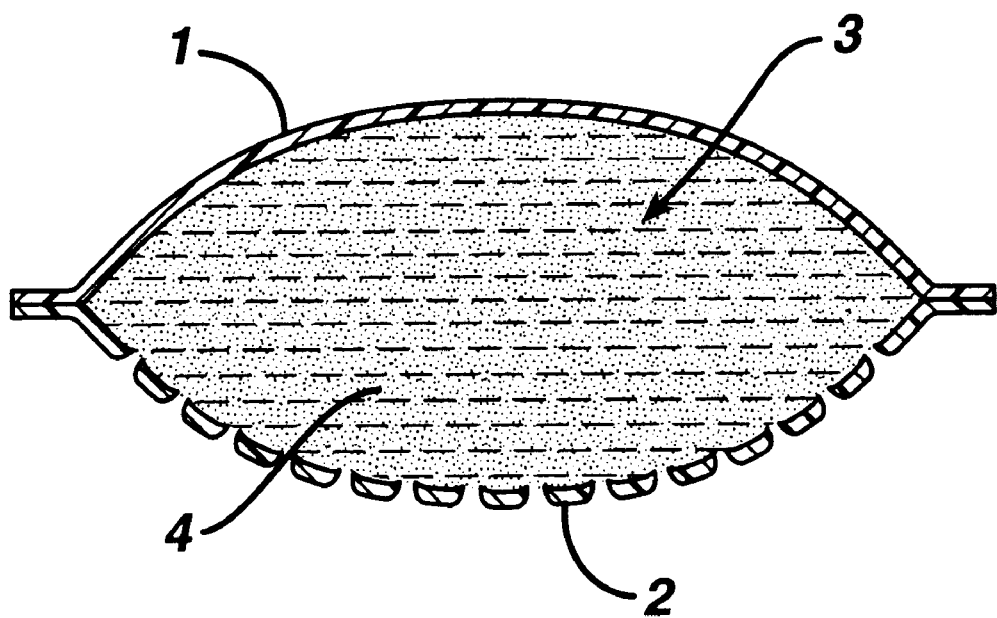
FIG. 5 illustrates a cross section view of FIG. 1 along line a which includes the topical skin care agent.
Figure 7:
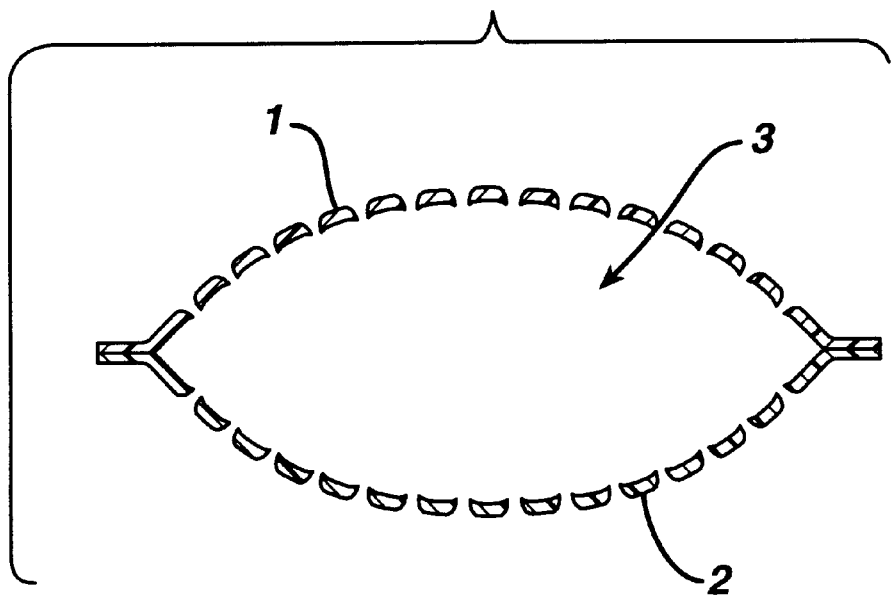
FIG. 7 illustrates a cross-sectional view of FIG. 6 along line b.
Figure 8:
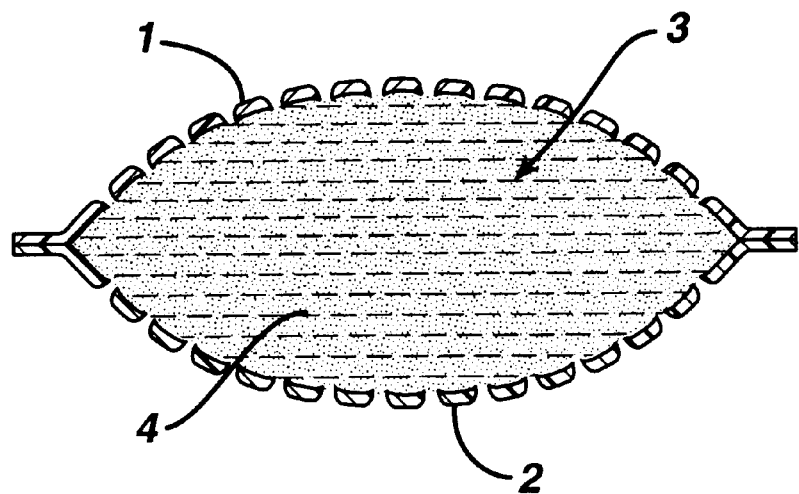
FIG. 8 illustrates a cross-sectional view of FIG. 6 along line b which includes the topical skin care agent.

In the delivery systems of the invention, the rough side of the film faces the pouch portion of the delivery system, as illustrated in FIG. 4 and FIG. 7. FIG. 4 illustrates a cross sectional view along line a of FIG. 1. FIG. 7 illustrates a cross sectional view along line b of FIG. 6. Only the bottom layer, 2, of the device illustrated in FIG. 4 comprise an aperatured film. The top layer, 1, and the bottom layer, 2, of the device illustrated in FIG. 7 comprise an apertured film. The rough side of the apertured films faces the pouch, 3, of the device. The topical skin care agent is not illustrated in FIG. 4 or FIG. 7 in order to more clearly illustrate the top layer and the bottom layer of these devices. FIG. 5 illustrates a cross sectional view along line a of FIG. 1, where the topical skin care agent, 4, is illustrated within pouch, 3, of the device. FIG. 8 illustrates a cross sectional view along line b of FIG. 6, where the topical skin care agent, 4, is illustrated within pouch, 3, of the device.

Both the top layer and the bottom layer of the delivery system of the invention may comprise apertured films, however, if only one layer is an apertured film, the other layer may be made from any porous materials. Other suitable materials of construction for the top layer and the bottom layer include, but are not limited to natural fiber and synthetic fiber nonwoven materials, polyethylene films, and polypropylene films. The nonwoven materials may be hydrophobic or hydrophilic. An example of a natural fiber hydrophobic nonwoven material is cotton. Examples of synthetic fiber hydrophobic nonwoven materials include, but are not limited to, rayon and polypropylene. The nonwoven material may contain more than one component and may be prepared by various processes known in the art. Bicomponent spunbond nonwoven materials, which make a web like pattern are preferred. Suitable nonwovens are commercially available, for example through PGI Nonwovens. Examples of such nonwovens include, but are not limited to PGI 6757, PGI 67DCO, and PGI 6705.

In addition, the top layer and the bottom layer may comprise a number of the fabrics. For example the top layer may comprises an apertured film and a second fabric which is selected from natural fiber and synthetic fiber hydrophobic nonwoven materials as described above. The second fabric may be laminated to the apertured film. Alternatively, the second fabric may be sewed or layed over the apertured fabric. The second fabric may be placed on either the rough face or the smooth face of the apertured film. However, the preferred location of the second fabric is on the smooth face of the film.

As used herein, the term "topical skin care agent", refers to medicinal and cosmetic agents, which are dispersable in water, and which are used to topically treat the skin. Typical cosmetic agents include but are not limited to humectants, emollients, and vitamins. Typical medicinal agents include but are not limited to oatmeal, bicarbonate of soda, colloidal oatmeal, oilated colloidal bath treatment, surfactant based colloidal oatmeal cleanser, other cleanser systems, soy powder, herbal medicines and combinations thereof. Although these agents are available in solid and liquid formulations, the preferred formulation of said topical skin care agents is a solid formulation.

Further, topical skin care agents may include herbal medicines and combinations thereof may be included in the invention. The herbal medicine may treat more than one condition. Suitable herbal medicines include, but are not limited to, antifungal agents such as Centaurea Cyanus, Kalmia Latifolia and the like; antihistamine agents such as Mandragora Vernalis, Tanacetum Parthenium and the like; anti-infective agents such as Acacia Catechu, Aloe Barbadensis, Convallaria Majalis, Echinacea, Eucalyptus, Mentha Piperita, Rosa Canina, Sassafras Albidum, and the like; anti-inflammatory agents such as Fragaria Vesca, Matricaria Chamomilla, Salvia Officinalis and the like; antipruritic agents such as Anagallis Arvensis, Oenothera Biennis, Verbena Officinalis and the like; skin and mucous membrane agents such as Aesculus Hippocastanum, Avena Sativa, Baptista Tinctoria, Digitalis Purpurea, Hamamelis Virginiana, Helianthus Annuus, Hypericum Perforatum, Lawsonia Inermis, Nerium Odoratum and the like; and wound care agents such as Calendula Officinalis, Cinnamomum Verum, Coffea Arabica, Cola Acuminata, Solidago Species and the like. The preferred topical skin care agent is colloidal oatmeal.

As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, Beacon Colloidal oatmeal and Promix Colloidal Oatmeal.

The amount of topical skin care agent which is contained in the delivery systems of the invention, varies depending upon the type of agent used. Typically, the delivery systems of the invention contain from about 1 gram to about 100 grams of the topical skin care agent. Preferably the delivery systems contain from about 10 grams to about 50 grams, more preferably from about 15 grams to about 45 grams of the topical skin care agent.

Although the topical skin care agent of the invention may be placed directly in the pouch of the delivery system, these agents may be initially contained within a water soluble film which includes but is not limited to, polyvinyl alcohol polyvinyl acetate, and cellulose. This contained topical skin care agent may be in turn directly inserted into the pouch of the delivery system of the invention.

Typically, the delivery systems of the invention are exposed to bath water by funneling the water through the sachet while the bath is being drawn. This method results in the complete dispersion, dissolution and delivery of the topical skin care products contained within the pouch of the delivery system.

In one embodiment of the present invention, the top layer and the bottom layer are apertured films. In a second embodiment of the present invention, one layer is an apertured film and the other layer is a natural fiber or synthetic fiber hydrophobic nonwoven material. In yet a third embodiment of the invention, topical skin care agent is contained in a water-soluble film.

The delivery systems of the invention may be made in any shape, where those shapes which include but are not limited to, round, oval, rectangular, square, and triangular devices. The size of the article of the invention may be adapted to accommodate the amount of topical medicinal and skin care products to be delivered. Generally, a square article of the invention may range in size from 5 cm×5 cm to 15 cm×15 cm, preferably from 7.5 cm×7.5 cm to 12.5 cm×12.5 cm. A circular article of the invention may range in outer diameter from 5 cm to 20 cm, preferably from 7.5 cm to 17.5 cm, more preferably from 10 cm to 15 cm.

The following examples are intended to demonstrate possible delivery system of the invention. The examples should not be construed as limiting the scope of the invention.

EXAMPLE 1

Preparation Of Pouches Utilizing Apertured Films

For Sample A, an 11 cm×11 cm square pouch was prepared utilizing Tredegar Vispore film lot 25181 (a nonwoven/apertured film laminate) as the top and bottom layer. The apertured films were oriented so that the protuberances (rough side) faced the inside of the pouch. The apertured films were attached to each other on 3 sides by heat sealing. The pouch was filled with 21 grams of Beacon colloidal oatmeal. The pouch was then heat sealed on the 4th side. For Sample B, the process of Sample A was repeated except Tredegar Vispore film lot 25178 (a nonwoven/apertured film laminate) was substituted for lot 25181.

For Sample C, the process of Sample A was repeated except Promix colloidal oatmeal was substituted for Beacon colloidal oatmeal. For Sample D, the process of Sample A was repeated except Promix oatmeal with a particle size of 75 micrometers was substituted for Beacon colloidal oatmeal. Sample E was Promix colloidal oatmeal without a pouch. Sample F was Beacon colloidal oatmeal without a pouch. Samples D, E, and F were comparative Samples.

EXAMPLE 2

Reversed Orientation of Protuberances

Sample G was a pouch prepared as in Sample A above, except the protuberances were oriented towards the outside of the article.

EXAMPLE 3

Effect of Film On Dispersion

The effect of the number of apertures per square centimeter of film on dispersion of colloidal oatmeal was tested. Samples were prepared as in Sample A above, except the Tredegar film was varied to provide different numbers of apertures per square centimeter of film. Sample H contained 40 apertures per square centimeter. Sample I contained 22 apertures per square centimeter.

EXAMPLE 4

Dispersion Testing

The pouches prepared in Examples 1, 2, 3, and 4 were tested for dispersion of the colloidal oatmeal in water. The test was performed in a sink. A pouch was placed in the empty sink under a faucet with the water running at full force over the pouch. The water temperature was from 35° C. to 40° C. The pouch was agitated under the water, and the time for the colloidal oatmeal to dissolve and disperse from the pouch was measured. Samples were considered to fail if the colloidal oatmeal did not completely disperse without squeezing the pouch within 3 minutes. The results are reported in Table 1.

TABLE 1

| Sample | Result |
|--------|--------|
| A | Pass - Completely dispersed within two minutes. |
| B | Pass - Completely dispersed within one and one half minutes. |
| C | Pass - Completely dispersed within two and one half minutes. |
| D | Failed - After 3 minutes, 50% oatmeal remained in pouch. |
| E | Failed - 75% dispersed, large particles floating, some settling. |
| F | Failed - 75% dispersed, slight clumping, some settling. |
| G | Failed - required manual extrusion to release oatmeal. |
| H | Pass - Completely dispersed within one and one half minutes. |
| I | Pass - Completely dispersed within one minute. |

The data above demonstrates that the delivery system of the present invention provides less mess and more convenience than the current delivery systems for topical medicinal and skin care products. The number of apertures per square centimeter affects the dispersion rate of the topical skincare agents products, but the films tested both passed the test for dispersion.

We claim:

1. A delivery system comprising:

a topical skin care agent, a top layer, and a bottom layer, where said top layer and said bottom layer comprise an apertured film having protuberances therein, where said top layer and said bottom layer are attached to each other leaving a pouch between said top layer and said bottom layer, where said protuberances of said apertured film face said pouch, and where said pouch contains said topical skin care agent, wherein, said top layer and said bottom layer comprise an apertured film having a bicomponent spunbond nonwoven material laminated to said apertured film and said topical skin care agent is collodial oatmeal, and said topical skin care agent is contained in a water soluble film selected from the group consisting of polyvinyl alcohol, polyvinyl acetate, and cellulose derivatives.

2. The delivery system of claim 1 wherein said top layer and said bottom layer comprise an apertured film which is laminated to a natural fiber or a synthetic fiber hydrophobic nonwoven material.

3. The delivery system of claim 1 wherein the apertures of either said top layer or said bottom layer have a size ranging from about 50 microns to about 75 microns.

4. The delivery system of claim 1 wherein the number of apertures per square centimeter of film of either said top layer or said bottom ranges from about 10 to about 50 apertures.

5. The delivery system of claim 1 wherein the number of apertures per square centimeter of film of either said top layer or said bottom layer ranges from about 15 to about 40 apertures.

* * * * *